United States Patent [19]

Landymore et al.

[11] Patent Number: 4,753,244
[45] Date of Patent: Jun. 28, 1988

[54] ENCAPSULATED MICROELECTRONIC HEART MONITOR

[76] Inventors: Roderick W. Landymore, R.R. #2, Spruce Court, Three Fathom Harbour, Nova Scotia, Canada, B0J 1N0; Allan E. Marble, 6366 South Street, Halifax, Nova Scotia, Canada, B3H 1T9; Donald W. Church, 6264 Summit Street, Halifax, Nova Scotia, Canada, B3L 1R7

[21] Appl. No.: 74,240

[22] Filed: Jul. 16, 1987

[30] Foreign Application Priority Data

Jun. 23, 1987 [CA] Canada ............................ 540298

[51] Int. Cl.⁴ .............................................. A61B 5/04
[52] U.S. Cl. .................................... 128/696; 128/642
[58] Field of Search ........................ 128/642, 695, 696

[56] References Cited

U.S. PATENT DOCUMENTS

| | | | |
|---|---|---|---|
| 3,144,018 | 8/1964 | Heap | 128/642 |
| 3,212,496 | 10/1965 | Preston | 128/903 |
| 3,682,162 | 8/1972 | Colyer | 128/642 |
| 3,826,244 | 7/1974 | Sallman et al. | 128/642 |
| 4,402,323 | 9/1983 | Whits | 128/642 |

Primary Examiner—William E. Kamm
Attorney, Agent, or Firm—Killworth, Gottman, Hagan & Schaeff

[57] ABSTRACT

Self-contained, micro-electronic heart monitor for mounting on or near the heart during surgery, to monitor the electrical activity of the heart during cardioplegic arrest by picking up and amplifying electrical signals from the heart and displaying an output when the signal exceeds a threshold level.

13 Claims, 2 Drawing Sheets

ENCAPSULATED MICROELECTRONIC HEART MONITOR

FIELD OF THE INVENTION

The present invention relates to an encapsulated microelectronic heart monitor which monitors the electrical status of the heart during cardioplegic arrest. Such a monitoring device is useful in regulating the volume of cardioplegic solution that is required to ensure a complete electrical arrest during heart surgery.

BACKGROUND OF THE INVENTION

Acquired and congenital defects of the heart are now routinely repaired through surgery in cardiac centres in North America. Such repair has become possible because of the development of a technique termed cardioplegia. Cardioplegia refers to the arresting of the heart by the infusion of a chemical solution into the heart by way of the ascending thoracic aorta. The most commonly used cardioplegic solution is a crystalloid solution of high potassium concentration and which solution is maintained at a temperature of 4°-8° C. The infusion of the solution induces a rapid cardiac arrest. The cardiac arrest is essential as it provides a quiet and bloodless operating field for the surgeon and prevents the utilization of high energy phosphate stores by preventing useless electromechanical work. The cold cardioplegic solution also lowers myocardial temperature which is desirable. The cessation of electromechanical activity and the reduction of myocardial temperature reduce the risk of myocardial injury during the performance of cardiac surgery.

Temperature monitoring and multiple dose cardioplegia are now widely used to maintain an electromechanical arrest and to prevent rewarming. Despite this, myocardial injury is still observed following electrocardiac arrest.

SUMMARY OF THE INVENTION

It has now been discovered in connection with the present invention that small amplitude electrical potentials exist in the myocardium after the infusion of the cardioplegic solution when all electromechanical activity has ceased and the conventional electrocardiogram is isoelectric. This was described in Landymore et al, "Spectral Analysis of Small-Amplitude Electrical Activity in the Cold Patassium-Arrested Heart", The Annals of Thoracic Surgery, Volume 41, Number 4, April, 1986 and in Marble et al, "Measurement and Spectral Analysis of Fibrillation in the Normothermic and Hypothermic Myocardium'8 , Medical and Biological Engineering and Computing, November, 1986. It has also been discovered that such persistent electrical activity is associated with myocardial injury after elective cardiac arrest. This discovery is described in Landymore et al, "Effect of Small-Amplitude Electrical Activity on Myocardial Preservation in the Cold Potassium-Arrested Heart", The Journal of Thoracic and Cardiovascular Surgery, Vol. 91, No. 5, pp. 684-689, May, 1986. If the occurrence of this small amplitude electrical activity was known, additional cardioplegic solution could be administered to promote complete electrical inactivity. It is therefore desirable to monitor the electrical status of the heart for electrical activity during cardioplegic arrest. The monitoring would serve to determine the volume and frequency of the infusion of cardioplegic solution to ensure complete electrical arrest during cardiac surgery.

It is known in the prior art to monitor heart activity through an electrocardiogram where electrodes are placed on the skin and signals are transmitted through conductors to the monitoring equipment. This method as has been discovered is not of sufficient sensitivity to detect the small amplitude electrical signals which could be present during elective cardiac arrest. U.S. Pat. No. 4,562,846, granted on Jan. 7, 1986 teaches the use of placing plunge electrodes into the heart and connecting these by conductors to monitoring equipment including a digital computer and display located in the operating room. There are serious technical difficulties in detecting small amplitude electrical potentials utilizing the method taught in U.S. Pat. No. 4,562,846 due to electrical and mechanical interference which mask the desired signals. In the context of the present invention it was realized that to record the small amplitude electrical potentials from the myocardium, extraordinary precautions were necessary. In order to obtain a reliable signal it was necessary to ground all electrical equipment, to ground the animal's bloodstream, to filter out 60 Hz electrical interference and to use a nonpulsatile pump for cardiopulmonary bypass as described in the first Landymore publication referred to above. There was always the risk that unknown and uncompensated interference would occur during surgery and render unreliable the myocardium signal recording. Also the conductors connecting the monitoring equipment to the patient's heart impede movement about the patient by operating room personnel. There was always the danger that someone would trip on a conductor thus disconnecting it or possibly causing injury to the patient or operating room personnel. The long conductors and the associated monitoring equipment were not satisfactory for operating room efficiency and safety.

Accordingly, the present invention provides a self-contained device for mounting on or near the heart during surgery for monitoring the electrical activity of the heart during cardioplegic arrest, comprising; plunge electrode means for mounting said device on or near the heart and for picking up potentials from the heart; power supply means; microvoltage signal amplification means for amplifying potentials picked up by said plunge electrode: and display means responsive to said amplification means for indicating the presence of said potentials.

BRIEF DESCRIPTION OF THE DRAWINGS

The present invention will be better understood through the following detailed description of a preferred embodiment in conjunction with the accompanying drawings in which.

DETAILED DESCRIPTION OF THE PREFERRED EMBODIMENT

Figure 1:
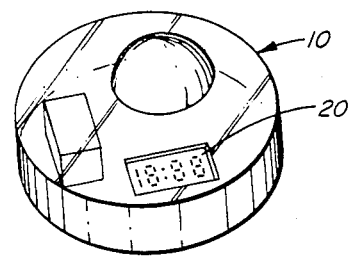
FIG. 1 is a top view of the preferred embodiment of the invention.

FIG. 1 is a top view of the preferred embodiment of the invention showing the main body 10 of the invention formed by encapsulating the microelectronic circuitry, power supply and display of the electrical activity in the heart. If no electrical activity is present the display will be blank. The main body of the preferred embodiment is cylindrical in shape having a diameter of approximately 29 mm and a thickness of approximately 8 mm, although the shape and dimensions are not critical.

Figure 2:
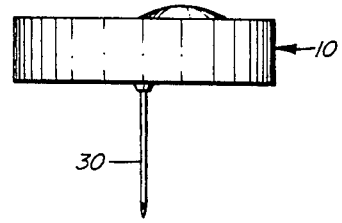
FIG. 2 is a side view of the preferred embodiment of the invention.

FIG. 2 is a side view of the preferred embodiment. Attached to the main body 10 is a plunge electrode 30 which is inserted into the heart. plunge electrodes are well-known and can be comprised of a stainless steel hypodermic needle with a length of 30 AWG/KYNAR insulated wire epoxied inside of it. The electrode picks up the signals from the myocardium and transmits the signal to the encapsulated circuitry. The stainless steel needle which is insulated along its length except for the active bipolar electrodes, serves as a shield and also as the ground return for the signal.

Figure 3:
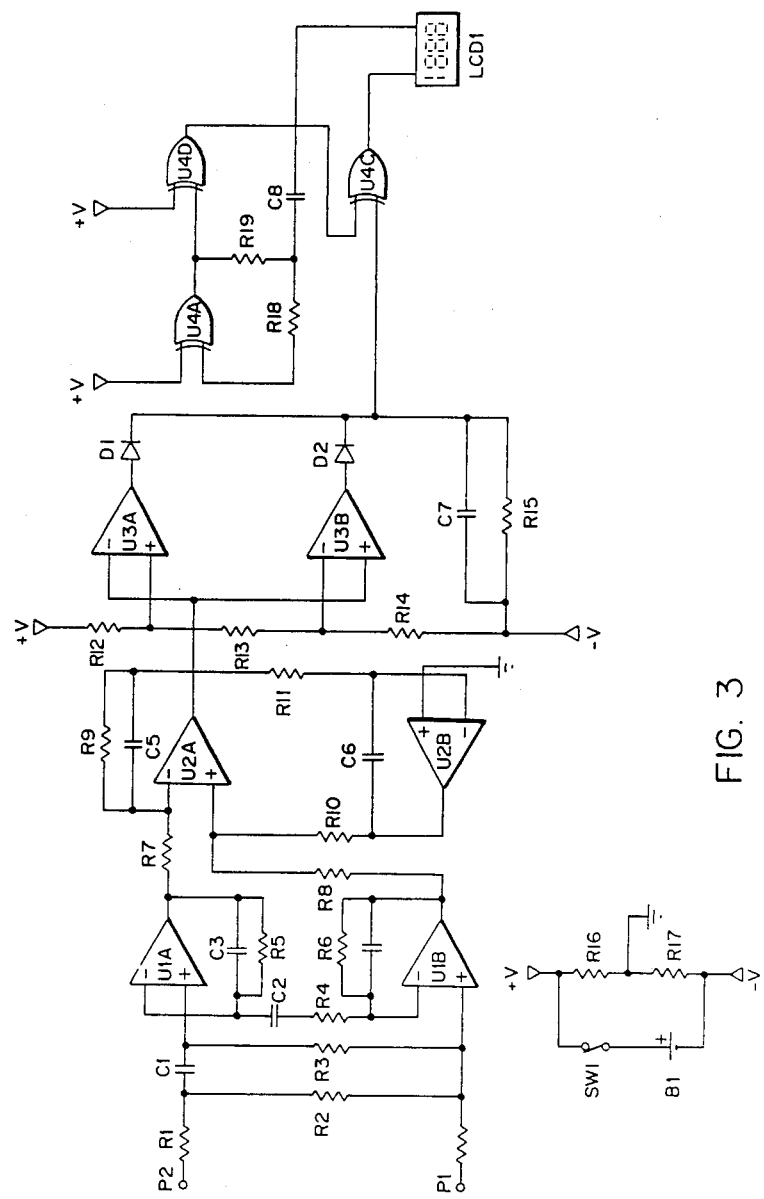
FIG. 3 is a schematic drawing of the microelectronic circuitry of the preferred embodiment.

FIG. 3 shows in schematic form the microelectronic circuit of the preferred embodiment. The signals generated in the myocardium are in the microvolt range. The monitor uses low power CMOS operational amplifiers to condition and monitor the said signals. The power supply B1 is a single lithium battery which is encapsulated with the circuitry in the main body of the monitor. SW1 is a normally closed reed switch in series with the battery. A small magnet on the top surface of the monitor maintains SW1 in an open condition when the monitor is not being used. When it is desired to use the monitor, the small magnet is removed and SW1 closes and connects the commercially available lithium battery to the microelectronic circuit. The said battery is capable of providing sufficient power to operate the monitor continuously for 20 days.

The signal from the heart is introduced into the monitor's microelectronic circuitry at inputs P1 and P2. Components R1, R2, R3 and C1 form a passive low frequency decoupling circuit which provides isolation protection and a suitable input impedance. C1 removes the large dc component of the heart signal.

Operational amplifiers U1A, U1B and U2A are configured together with components R4, R5, R6, R7, R8, R9, R10, C2, C3, C4 and C5 as a frequency selective differential amplifier with a bandwidth of approximately 0.5 Hertz to 30 Hertz. Amplifier U2B, C6 and R11 comprise an autozeroing circuit to remove dc offsets. Operational amplifiers U3A and U3B and components R12, R13 and R14 form a window detector with the width of the window varying from 6 to 600 microvolts depending on the value of R13. This circuit operates as a precision full-wave rectifier and threshold detector. The threshold is determined by the value of R13. When the signal exceeds the threshold value, either positive or negative, diode D1 or D2 will be forward biased and capacitor C7 will charge toward V+. When the voltage across capacitor C7 reaches the threshold level for gate U4C, the said gate turns on and connects the output from a low frequency oscillator comprised of components U4A, U4D, C8, R18 and R19 to the liquid crystal display LCD1. A number will appear on the liquid crystal display. When C7 is fully charged the input signal from the heart will have to drop below the threshold for a period of at least one second before the display will switch off. When the monitor is not in use the small magnet is returned to the surface of the monitor, opening reed switch SW1 and disconnecting the battery power supply from the microelectronic circuitry.

It may be necessary to use more than one monitor during operations and because of the small size this is possible.

Furthermore there may be surgical conditions where it is preferable not to locate the monitor on the heart but very close to it. This is particularly the case where the heart is to be manipulated during surgery.

Figure 4:
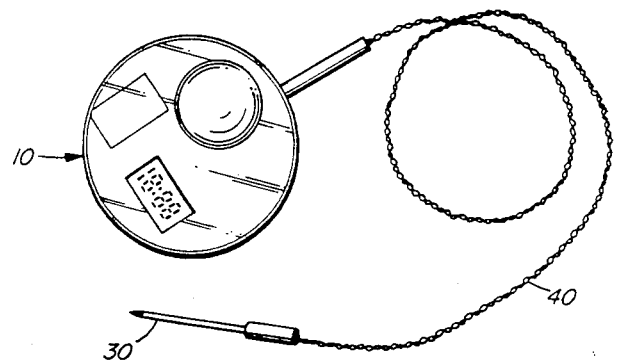
FIG. 4 is a top view of second preferred embodiment of the invention which enables the monitor to be placed near the heart rather than on it.

FIG. 4 is a top view of the preferred embodiment which permits the main body 10 of the invention to be located near the heart rather than being mounted on the heart. The plunge electrode 30 is not mounted directly on the main body as was the case in the embodiment of FIG. 2 but is connected to the main body by a flexible twisted pair conductor, 40. The flexibility is required because an inflexible conductor would interfere with heart manipulation.

The length of the conductor 40 must be limited to ensure that the levels of induced undesirable signals are kept to a magnitude which will not mask the signals from the heart and to ensure an efficient and safe operating environment.

The unwanted induced voltages in the leads should be at least 2 orders of magnitude and preferably 3 orders of magnitude less than the potentials being measured in the myocardium.

Considering that there are two leads in the conductor 40, and assuming the length of each lead to be 15 cm, which together form a loop, the voltage induced into that loop by a current carrying wire a reasonable distance away from the loop can be estimated. If one assumes that the loop is such that its perimeter is 30 cm with a spacing of 1 mm, the area of the loop is calculated to be 1.5 cm$^2$. A wire located 1 m from the loop and carrying a current of 1 ampere would create a magnetic field intensity in the loop of a magnitude given by:

$$B = \frac{\mu_o NI}{2\pi r}$$

where
  $\mu_o$ is the permeability of free space
  N is the number of turns of the current carrying wire (here N=1)
  I is the current in the wire (here I=1 ampere)
  r is the distance between the current carrying wire and the loop
  $B = 2 \times 10^{-7} \sin 377 \omega t$ webers/m$^2$ The magnetic flux $\phi$ is given by:

$$\phi = BA$$

where
  B is the magnetic field intensity
  A is the area of the loop (here A=1.5 cm$_2$)
  $\phi = 3 \times 10^{-11} \sin 377 \omega t$ webers The voltage induced in the loop is given by:

$$e = \frac{Nd\phi}{dt}$$

N is the number of turns in the loop (here N =1)
$e = 1.1 \times 10^{-8} \cos 377 \omega t$ volts The voltage induced in the said leads would be 0.011 microvolts which is three orders of magnitude less than the signal to be detected from the myocardium and is acceptable.

There may be situations where longer leads can be used depending upon the source or sources of interference but the induced signal ought to be at least 2 orders of magnitude less than the signal to be measured from the myocardium. As a practical matter, leads in excess of 15 cm are not desirable because they physically interfere with the surgeon and operating room personnel, resulting in reduced efficiency and safety.

Other electronic circuitry, display devices, configurations and modifications are possible without departing from the invention.

The embodiments of the invention in which an exclusive property or privilege is claimed are defined as follows:

1. A self-contained device for mounting on the heart during surgery for monitoring the electrical activity of the heart during cardioplegic arrest, comprising: plunge electrode means for mounting said device on the heart and picking up potentials from the heart; power supply means; microvoltage signal amplification means for amplifying potentials picked up by said plunge electrode; and display means responsive to said amplification means for indicating the presence of said potentials.

2. The device of claim 1 in which the plunge electrode is rigidly protruding from the device and comprised of a rigid hollow cylindrical outer electrical conductor and a wire inner conductor electrically insulated from the outer conductor.

3. The device of claim 2 in which the plunge electrode is comprised of a length of number 30 AWG kynar insulated wire epoxied into a hypodermic needle.

4. The device of claim 1 in which the microvoltage signal amplification means is comprised of low power CMOS integrated circuits.

5. The device of claim 1 in which the microvoltage signal amplification means is comprised of low power CMOS integrated circuits and the power supply means is a single lithium battery.

6. The device of claim 1 in which the power supply means, microvoltage signal amplification means and display means are encapsulated in a plastic body with at least that portion of the body overlying the display means being clear and the power supply means is electrically connected to the microvolt signal amplifying means and display means by a normally closed reed switch which is opened by the placement of a magnet on the surface of the device.

7. A self-contained device for mounting near the heart during surgery for monitoring the electrical activity of the heart during cardioplegic arrest, comprising: plunge electrode means for picking up voltages from the heart; power supply means; microvoltage signal amplification means for amplifying potentials picked up by said plunge electrode; display means responsive to said amplification means for indicating the presence of said potentials; and flexible connecting means electrically connecting the plunge electrode to the microvoltage signal amplification means, which flexible connecting means is configured so as to maintain induced voltages at a level of at least two orders of magnitude lower than the myocardial potentials being monitored.

8. The device of claim 7 in which the flexible connecting means is configured so as to maintain induced voltages at a level of at least three orders of magnitude lower than the myocardial potentials being monitored.

9. The device of claim 8 in which the microvoltage signal amplication means is comprised of low power CMOS integrated circuits and the power supply means is a single lithium battery.

10. The device of claim 7 in which the plunge electrode is comprised of a length of number 30 AWG KYNAR insulated wire epoxied into a hypodermic needle.

11. The device of claim 7 in which the microvoltage signal amplification means is comprised of low power CMOS integrated circuits.

12. The device of claim 7 in which the power supply means, microvoltage signal amplication means and display means are encapsulated in a plastic body with at least that portion of the body overlying the display means being clear and the power supply means is electrically connected to the microvolt signal amplification means and display means by a normally closed reed switch which is opened by the placement of a magnet on the surface of the device.

13. The device of claim 7 in which the flexible connecting means is comprised of a twisted pair of electrical leads of which each lead is no longer than 15 cm.

* * * * *